(12) United States Patent
Tai et al.

(10) Patent No.: US 9,320,912 B2
(45) Date of Patent: Apr. 26, 2016

(54) DEEP MAGNETIC FIELD GENERATING APPARATUS

(71) Applicants: National Cheng Kung University, Tainan (TW); Metal Industries Research & Development Centre, Kaohsiung (TW)

(72) Inventors: Cheng-Chi Tai, Tainan (TW); Shyh-Jier Huang, Tainan (TW); Xi-Zhang Lin, Tainan (TW); Chien-Chang Chen, Kaohsiung (TW); Tsung-Chih Yu, Tainan (TW)

(73) Assignees: National Cheng Kung University, Tainan (TW); Metal Industries Research & Development Centre, Kaohsiung (TW)

( * ) Notice: Subject to any disclaimer, the term of this patent is extended or adjusted under 35 U.S.C. 154(b) by 22 days.

(21) Appl. No.: 13/765,277

(22) Filed: Feb. 12, 2013

(65) Prior Publication Data
US 2014/0081069 A1    Mar. 20, 2014

(30) Foreign Application Priority Data
Sep. 14, 2012   (TW) .............................. 101133801 A

(51) Int. Cl.
*A61N 2/00* (2006.01)
*A61N 2/02* (2006.01)

(52) U.S. Cl.
CPC . *A61N 2/02* (2013.01); *A61N 2/004* (2013.01)

(58) Field of Classification Search
CPC ......... A61N 2/002; A61N 2/004; A61N 2/02; A61N 2/06; A61N 2/008; A61N 2/006; A61N 1/36021; A61N 1/36025; A61N 1/36028; A61N 2001/36039; H01F 5/00; H01F 5/06; H01F 27/288; H01F 27/289; H01F 27/2895
USPC ................................ 600/9–15; 607/100, 103
See application file for complete search history.

(56) References Cited

U.S. PATENT DOCUMENTS

| | | | | |
|---|---|---|---|---|
| 5,000,178 | A * | 3/1991 | Griffith | 607/2 |
| 5,314,401 | A * | 5/1994 | Tepper | 600/14 |
| 5,951,459 | A * | 9/1999 | Blackwell | 600/13 |
| 6,569,078 | B2 * | 5/2003 | Ishikawa et al. | 600/9 |
| 7,976,453 | B2 * | 7/2011 | Zimmerling et al. | 600/25 |
| 2005/0182287 | A1 * | 8/2005 | Becker | 600/13 |
| 2008/0097141 | A1 * | 4/2008 | Kolt | 600/13 |

FOREIGN PATENT DOCUMENTS

TW          201112883 A1    4/2011

* cited by examiner

*Primary Examiner* — Charles A Marmor, II
*Assistant Examiner* — Carrie R Dorna
(74) *Attorney, Agent, or Firm* — Muncy, Geissler, Olds & Lowe, P.C.

(57) ABSTRACT

A deep magnetic field generating apparatus includes a first coil unit and a second coil unit. The second coil unit is connected with the first coil unit, and disposed around the first coil unit horizontally. Accordingly, the deep magnetic field generating apparatus can generate a desired deep magnetic field.

9 Claims, 4 Drawing Sheets

DEEP MAGNETIC FIELD GENERATING APPARATUS

CROSS REFERENCE TO RELATED APPLICATIONS

This Non-provisional application claims priority under 35 U.S.C. §119(a) on Patent Application No(s). 101133801 filed in Taiwan, Republic of China on Sep. 14, 2012, the entire contents of which are hereby incorporated by reference.

BACKGROUND OF THE INVENTION

1. Field of Invention

The present invention relates to a generating apparatus and, in particular, to a deep magnetic field generating apparatus.

2. Related Art

The current tumor thermotherapy technologies include microwave thermotherapy, radiofrequency ablation (RFA) therapy, and high-intensity focused ultrasound (HIFU) therapy. Among these therapies, the microwave thermotherapy and RFA therapy are to directly insert a needle electrode into a tumor and then generate heat to cause coagulative necrosis of partial tumor tissue, thereby achieving the purpose of tumor therapy. Herein, the microwave thermotherapy is to generate heat by the microwave generator configured at the tip of the microwave electrode. The RFA therapy is to utilize the radiofrequency current of the electrode needle to excite ions so as to generate heat. However, the above-mentioned therapies are very expensive and will cause much pain to patients.

Accordingly, a novel electromagnetic thermotherapy, which is to apply an alternating magnetic field on an electromagnetic needle, has been disclosed. In this case, the alternating magnetic field induces the eddy current in the needle to generate heat for burning the tumor tissues. This thermotherapy can sufficiently decrease the treatment cost and the pain of patients. Obviously, the applied electromagnetic field is very important to this novel electromagnetic thermotherapy.

Therefore, it is an important subject of the invention to provide a deep magnetic field generating apparatus that can generate a deep magnetic field to improve the electromagnetic induction as well as the treatment quality.

SUMMARY OF THE INVENTION

In view of the foregoing subject, an objective of the present invention is to provide a deep magnetic field generating apparatus that can generate a desired deep magnetic field.

To achieve the above objective, the present invention discloses a deep magnetic field generating apparatus including a first coil unit and a second coil unit. The second coil unit is connected with the first coil unit, and disposed around the first coil unit horizontally.

In one embodiment, a diameter of the second coil unit ranges from 1.5 to 5 times of a diameter of the first coil unit.

In one embodiment, each of the first coil unit and the second coil unit comprises a coil or a plurality of coils connected in series, and the coils are the same or different.

In one embodiment, each of the first coil unit and the second coil unit comprises a single-turn coil, a multiple-turn concentric coil, a pancake coil, or their combinations.

In one embodiment, the deep magnetic field generating apparatus further comprises a magnetic-field limitation element. The material of the magnetic-field limitation element comprises a low permeability material. The first coil unit is at least partially disposed within the magnetic-field limitation element, and the second coil unit is wound around the magnetic-field limitation element.

In one embodiment, the magnetic-field limitation element comprises a top portion and an annular portion connected to one side of the top portion, and the first coil unit is disposed within the annular portion.

In one embodiment, the deep magnetic field generating apparatus further comprises a magnetic-field reinforcement element disposed in the magnetic-field limitation element. The first coil unit is at least partially wound around the magnetic-field limitation element.

In one embodiment, the material of the magnetic-field reinforcement element comprises a soft ferrite, a molypermalloy powder (MPP) core, a high flux (HF) powder core, or their combinations.

In one embodiment, the deep magnetic field generating apparatus further comprises two electrical joints. One of the electrical joints is connected to the first coil unit, and the other one is connected to the second coil unit.

As mentioned above, in the deep magnetic field generating apparatus of the invention, the inner first coil unit generates a concentrated magnetic field, while the outer second coil unit generates a large-area magnetic field. These two magnetic fields can together provide a deep magnetic field. Since the concentrated deep magnetic field can reach the deeper portion of human body, it can be applied to the electromagnetic needle for burning the deeper tumors. Accordingly, the treatment effect can be improved. Besides, the needed components are very simple, so the treatment cost is decreased.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1:
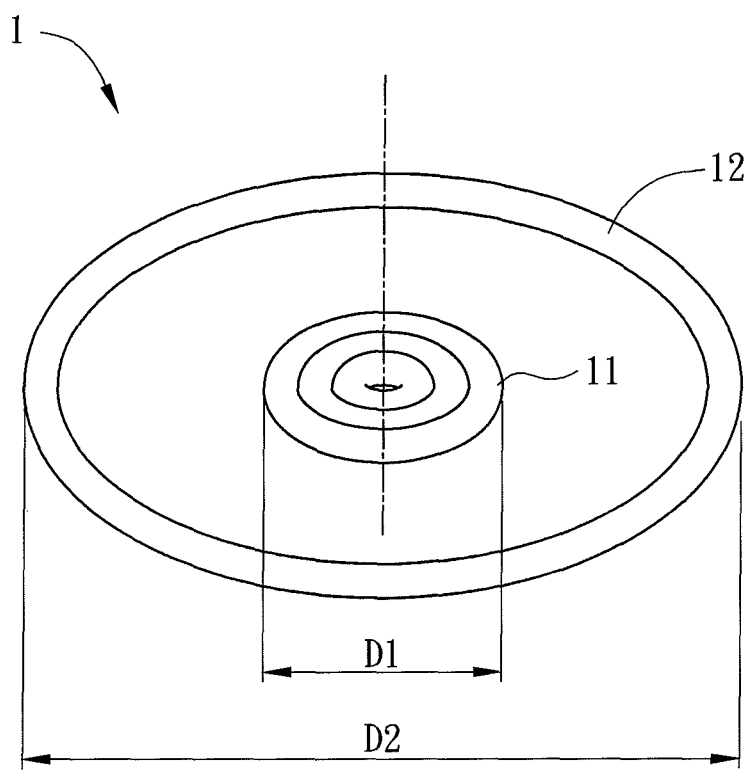
FIG. 1 is a schematic diagram showing a deep magnetic field generating apparatus according to a preferred embodiment of the invention.

FIG. 1 is a schematic diagram showing a deep magnetic field generating apparatus 1 according to a preferred embodiment of the invention. As shown in FIG. 1, the deep magnetic field generating apparatus 1 includes a first coil unit 11 and a second coil unit 12. The second coil unit 12 is connected with the first coil unit 11, and disposed around the first coil unit 11 horizontally. Accordingly, the inner first coil unit 11 generates a concentrated magnetic field, while the outer second coil unit 12 generates a large-area magnetic field, so that these two magnetic fields can together provide a deep magnetic field.

When the diameter of the second coil unit 12 is too large, the area occupied by the deep magnetic field generating apparatus 1 is also too large to apply in application. Besides, the large area also decreases the interaction between the magnetic fields generated by the first coil unit 11 and the second coil unit 12, so that the effect of the generated deep magnetic field is also weakened. Otherwise, when the diameter of the second coil unit 12 is too small, the range of the magnetic field generated by the second coil unit 12 is insufficient, which also weakens the effect of the generated deep magnetic field. In this embodiment, the diameter D2 of the second coil unit 12 preferably ranges from 1.5 to 5 times of the diameter D1 of the first coil unit 11. The first and second coil units within this range may provide better deep magnetic field.

This invention is not to limit the type of the first coil unit 11 and the second coil unit 12. For example, each of the first coil unit 11 and the second coil unit 12 may include a coil or a plurality of coils connected in series, and the coils are the same or different. Besides, each of the first coil unit 11 and the second coil unit 12 may include a single-turn coil, a multiple-turn concentric coil, a pancake coil, or their combinations. In this embodiment, the first coil unit 11 includes a plurality of coils connected in series, while the second coil unit 12 includes a single coil. The first coil unit 11 is connected to the second coil unit 12 (not shown). In practice, the first coil unit 11 is wound and then the second coil unit 12 is continuously wound around the first coil unit 11.

The deep magnetic field generating apparatus 1 may further include two electrical joints (not shown). One of the electrical joints is connected to the first coil unit 11, and the other one is connected to the second coil unit 12. The electrical joints are configured for electrically connecting to a power source so as to supply an AC power to the deep magnetic field generating apparatus 1.

Figure 2:
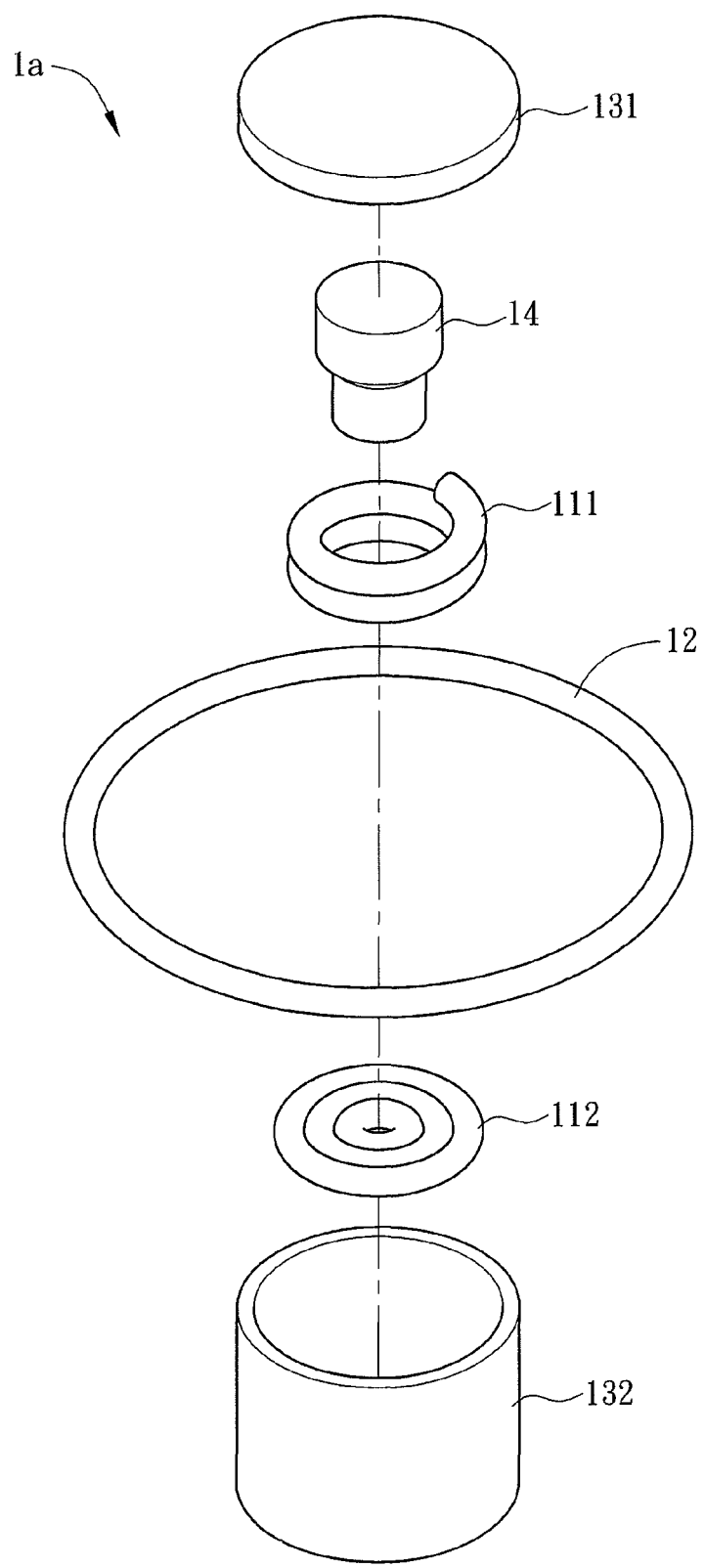
FIG. 2 is an exploded view of another deep magnetic field generating apparatus according to a preferred embodiment of the invention.
Figure 3:
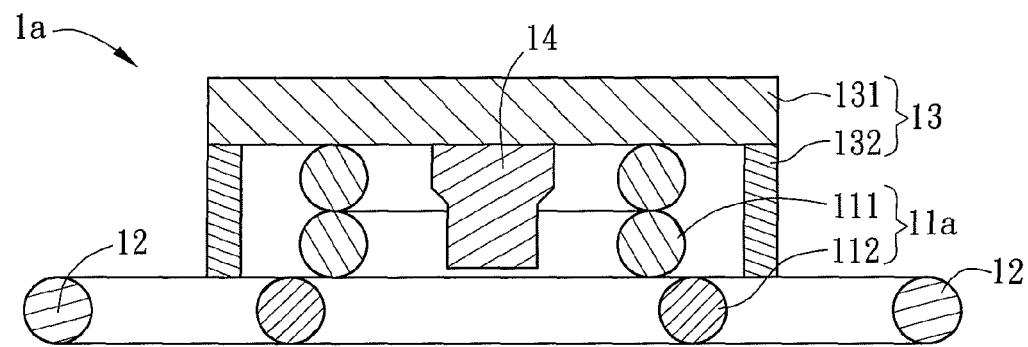
FIG. 3 is a schematic diagram showing the assembled deep magnetic field generating apparatus of FIG. 2.

FIG. 2 is an exploded view of another deep magnetic field generating apparatus 1a according to a preferred embodiment of the invention, and FIG. 3 is a schematic diagram showing the assembled deep magnetic field generating apparatus 1a of FIG. 2. Referring to FIGS. 2 and 3, the deep magnetic field generating apparatus 1a includes a first coil unit 11a and a second coil unit 12. The first coil unit 11a includes a plurality of coils 111 and 112, for example, and the coils 111 and 112 are different from each other. In this embodiment, the coil 111 is a multiple-turn concentric coil (e.g. a double-turn concentric coil), and the coil 112 is a pancake coil. Besides, the coils 111 and 112 are connected to each other.

In addition, the deep magnetic field generating apparatus 1a further includes a magnetic-field limitation element 13. The material of the magnetic-field limitation element 13 includes a low permeability material, which has relatively lower permeability. For example, the proper low permeability material has a relative permeability less than 100. In practice, some permeability materials such as Fluxtrol 50 and Fluxtrol 559H have a relative permeability less than 60. The first coil unit 11a is at least partially disposed within the magnetic-field limitation element 13, and the second coil unit 12 is wound around the magnetic-field limitation element 13. In this embodiment, the coil 111 of the first coil unit 11a is disposed within the magnetic-field limitation element 13.

In this embodiment, the magnetic-field limitation element 13 includes a top portion 131 and an annular portion 132 connected to one side of the top portion 131, and the first coil unit 11a is disposed within the annular portion 132. The shape of the magnetic-field limitation element 13 is not limited. The most important configuration is to dispose at least a part of the first coil unit 11a within the magnetic-field limitation element 13, so that the first coil unit 11a can generate a magnetic field with better concentration effect. The top portion 131 and the annular portion 132 can be integrally formed or be connected by way of adhering, locking or the likes.

Moreover, the deep magnetic field generating apparatus may further include a magnetic-field reinforcement element 14 disposed in the magnetic-field limitation element 13. The first coil unit 11a is at least partially wound around the magnetic-field limitation element 14. In this embodiment, the magnetic-field reinforcement element 14 is connected to the top portion 131 of the magnetic-field limitation element 13, and the coil 111 of the first coil unit 11a is wound around the magnetic-field reinforcement element 14. The magnetic-field reinforcement element 14 can properly increase the depth of the magnetic field generated by the first coil unit 11a. The material of the magnetic-field reinforcement element 14 includes a soft ferrite, a molypermalloy powder (MPP) core, a high flux (HF) powder core, or their combinations. The HF powder core has a relative permeability larger than 1000. Besides, the magnetic-field reinforcement element 14 may also include other materials with higher relative permeability (e.g. the relative permeability larger than 1000).

Of course, the deep magnetic field generating apparatus may have different aspects, which will be described hereinafter.

Figure 4:
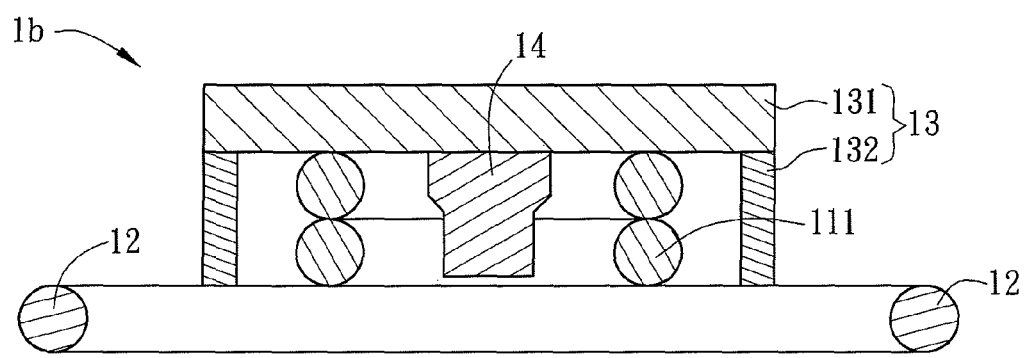
FIGS. 4 and 5 are schematic diagrams showing different aspects of the deep magnetic field generating apparatus according to the embodiment of the invention.

FIG. 4 is a schematic diagram showing another deep magnetic field generating apparatus 1b. Compared with the deep magnetic field generating apparatus 1a, the deep magnetic field generating apparatus 1b is not configured with the coil 112 (pancake coil) of the first coil unit 11a.

Figure 5:
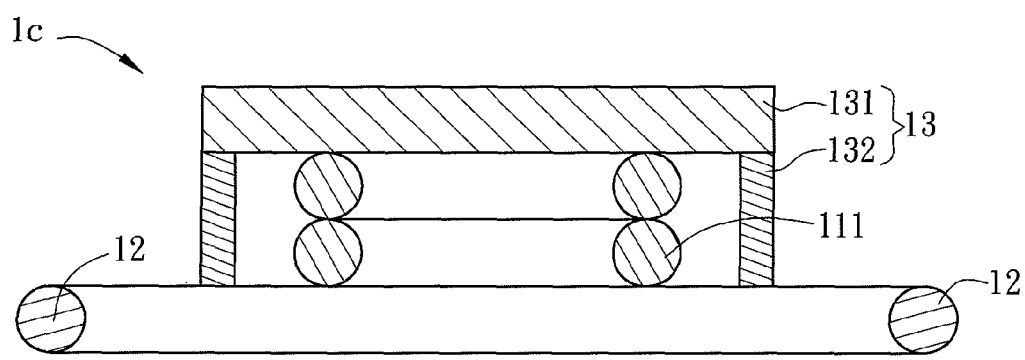

FIG. 5 is a schematic diagram showing another deep magnetic field generating apparatus 1c. Compared with the deep magnetic field generating apparatus 1b, the deep magnetic field generating apparatus 1c is not configured with the magnetic-field reinforcement element 14.

The application of any of the above-mentioned deep magnetic field generating apparatuses is not limited and includes the industrial or medical heating purpose. In this invention, the deep magnetic field generating apparatus cooperates with an electromagnetic needle and is applied to the medical heating application such as an electromagnetic thermotherapy.

Figure 6:
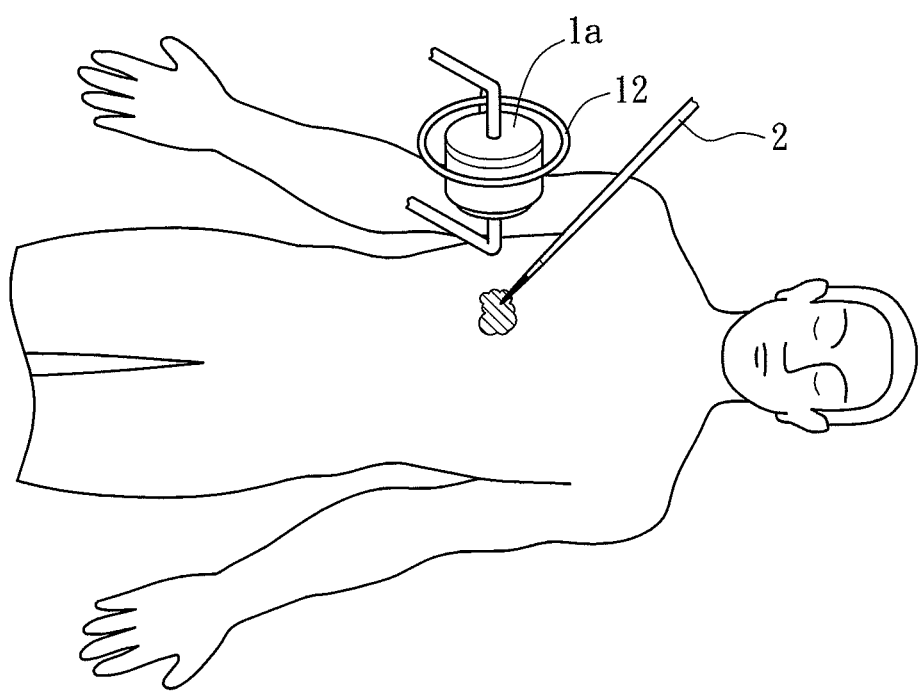
FIG. 6 is a schematic diagram showing an electromagnetic needle and the deep magnetic field generating apparatus of the invention.

FIG. 6 is a schematic diagram showing an electromagnetic needle 2 and the deep magnetic field generating apparatus 1a of the invention. Of course, the deep magnetic field generating apparatus 1a can be substituted by any of the above-mentioned deep magnetic field generating apparatuses. In practice, the electromagnetic needle 2 is inserted into the tumor tissue of a human body, and the deep magnetic field generating apparatus 1a is applied with an AC power so as to generate a concentrated deep magnetic field. Accordingly, the end portion of the electromagnetic needle 2 generates an eddy current so as to generate heat for burning the tumor tissue.

To sum up, in the deep magnetic field generating apparatus of the invention, the inner first coil unit generates a concentrated magnetic field, while the outer second coil unit generates a large-area magnetic field. These two magnetic fields can together provide a deep magnetic field. Since the concentrated deep magnetic field can reach the deeper portion of human body, it can be applied to the electromagnetic needle for burning the deeper tumors. Accordingly, the treatment effect can be improved. Besides, the needed components are very simple, so the treatment cost is decreased.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A deep magnetic field generating apparatus, comprising:
   a magnetic-field limitation element which comprises a top portion and an annular portion, wherein the annular portion is connected to one side of the top portion to form an accommodating space;
   a first coil unit having a first coil and a second coil, wherein said first coil is covered by said top portion, surrounded by said annular portion and accommodated in said accommodating space of the magnetic-field limitation element, and said second coil is not disposed within said accommodating space of the magnetic-field limitation element; and
   a second coil unit, which is connected with the first coil unit,
   wherein the first coil and the second coil are disposed along a direction perpendicular to a surface of the top portion of the magnetic-field limitation element, and the second coil does not overlap the second coil unit along the direction.

2. The deep magnetic field generating apparatus of claim 1, wherein a diameter of the second coil unit ranges from 1.5 to 5 times of a diameter of the first coil unit.

3. The deep magnetic field generating apparatus of claim 1, wherein the second coil unit comprises a coil or a plurality of coils connected in series.

4. The deep magnetic field generating apparatus of claim 3, wherein said plurality of coils are the same or different.

5. The deep magnetic field generating apparatus of claim 1, wherein each of the first coil unit and the second coil unit comprises a single-turn coil, a multiple-turn concentric coil, a pancake coil, or their combinations.

6. The deep magnetic field generating apparatus of claim 1, wherein the magnetic-field limitation element comprising a low permeability material, and the second coil unit is wound around the magnetic-field limitation element.

7. The deep magnetic field generating apparatus of claim 6, further comprising:
   a magnetic-field reinforcement element disposed in the magnetic-field limitation element, wherein the first coil unit is at least partially wound around the magnetic-field reinforcement element.

8. The deep magnetic field generating apparatus of claim 7, wherein the material of the magnetic-field reinforcement element comprises a soft ferrite, a molypermalloy powder (MPP) core, a high flux (HF) powder core, or their combinations.

9. The deep magnetic field generating apparatus of claim 1, further comprising:
   two electrical joints, wherein one of the electrical joints is connected to the first coil unit, and the other one of the electrical joints is connected to the second coil unit.

* * * * *